United States Patent
Jetti et al.

(10) Patent No.: US 10,479,782 B2
(45) Date of Patent: Nov. 19, 2019

(54) FORMS OF LUMACAFTOR AND PROCESSES FOR THE PREPARATION THEREOF

(71) Applicant: Mylan Laboratories LImited, Hyderabad (IN)

(72) Inventors: Ramakoteswara Rao Jetti, Hyderabad (IN); Hemant Malhari Mande, Hyderabad (IN); AnJaneyaraju Indukuri, Hyderabad (IN); Bommareddy Aggiramireddy, Hyderabad (IN); Neelima Bhagavatula, Hyderabad (IN); Amit Singh, Hyderabad (IN); Soumyajit Ghosh, Hyderabad (IN); Attanti Veera Venkata Srinivasarao, Hyderabad (IN); Umasankara Sastry Tummalapalli, Hyderabad (IN); Veera Venkata Satya Surya Appala Gosula, Hyderabad (IN)

(73) Assignee: Mylan Laboratories Limited (IN)

( * ) Notice: Subject to any disclaimer, the term of this patent is extended or adjusted under 35 U.S.C. 154(b) by 0 days.

(21) Appl. No.: 15/763,216

(22) PCT Filed: Sep. 28, 2016

(86) PCT No.: PCT/IN2016/050326
§ 371 (c)(1),
(2) Date: Mar. 26, 2018

(87) PCT Pub. No.: WO2017/056109
PCT Pub. Date: Apr. 6, 2017

(65) Prior Publication Data
US 2019/0055224 A1    Feb. 21, 2019

(30) Foreign Application Priority Data

Sep. 29, 2015 (IN) .......................... 5209/CHE/2015
Mar. 1, 2016 (IN) ............................. 201641007085

(51) Int. Cl.
*C07D 405/12* (2006.01)

(52) U.S. Cl.
CPC .................................. *C07D 405/12* (2013.01)

(58) Field of Classification Search
CPC ..................................................... C07D 405/12
See application file for complete search history.

(56) References Cited

U.S. PATENT DOCUMENTS 8,507,534 B2 * 8/2013 Keshavarz-Shokri ..................... C07D 405/12
514/338

FOREIGN PATENT DOCUMENTS

WO   WO-2017056031 A1 * 4/2017 ........... C07D 405/12

OTHER PUBLICATIONS

International Search Report for PCT/IN2016/050326, dated Apr. 6, 2017, 7 pages.
Written Opinion of the International Searching Authority for PCT/IN2016/050326, dated Apr. 6, 2017; 9 pages.

* cited by examiner

*Primary Examiner* — Amanda L Aguirre

(57) ABSTRACT

The present disclosure provides amorphous lumacaftor, amorphous solid dispersions of lumacaftor, crystalline lumacaftor acetic acid solvate, crystalline lumacaftor ethyl acetate solvate, and processes for the preparation thereof. The lumacaftor forms disclosed herein may be useful for the preparation of oral dosage forms for treating cystic fibrosis transmembrane conductance regulator (CFTR) mediated diseases.

5 Claims, 11 Drawing Sheets

FORMS OF LUMACAFTOR AND PROCESSES FOR THE PREPARATION THEREOF

CROSS-REFERENCE TO RELATED APPLICATIONS

This application is a U.S. National Stage application under 35 U.S.C. § 371 of International Patent Application No. PCT/IN2016/050326, filed Sep. 28, 2016, which claims the benefit of Indian provisional patent application No. 5209/CHE/2015 filed on Sep. 29, 2015 and Indian provisional patent application No. 201641007085 filed on Mar. 1, 2016, each of which is hereby incorporated by reference in its entirety.

FIELD OF THE INVENTION

The present invention relates generally to active pharmaceutical ingredients and more specifically to lumacaftor. In particular, an amorphous form of lumacaftor, an amorphous solid dispersion of lumacaftor, lumacaftor acetic acid solvate, and lumacaftor ethyl acetate solvate are disclosed. Processes for the preparation of each of the disclosed forms are also provided.

BACKGROUND OF THE INVENTION

Lumacaftor, chemically known as 3-(6-(1-(2,2-difluorobenzo[d][1,3]dioxol-5-yl)cyclopropanecarboxamido)-3-methylpyridin-2-yl)benzoic acid, has the structure depicted below as Formula I.

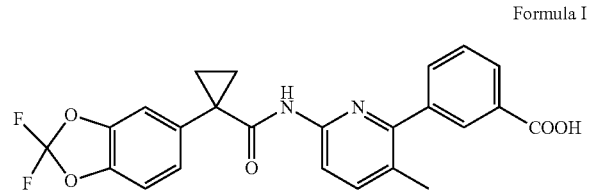 [SMILES: Cc1ccc(NC(=O)C2(c3ccc4c(c3)OC(F)(F)O4)CC2)nc1-c1cccc(C(=O)O)c1]

Formula I

Lumacaftor has been useful for treating or lessening the severity of a variety of cystic fibrosis transmembrane conductance regulator (CFTR) mediated diseases.

PCT application publication number WO2009/076142 discloses process for the preparation of lumacaftor and its intermediates.

PCT application publication number WO2009/073757 discloses lumacaftor form I. PCT application publication number WO2011/127290 discloses lumacaftor solvate Form A and the hydrochloric acid salt of lumacaftor solvate Form A.

The present disclosure provides amorphous lumacaftor as well as an amorphous solid dispersion of lumacaftor. Several solvates of lumacaftor, including lumacaftor acetic acid solvate, and lumacaftor ethyl acetate solvate, are also disclosed. Processes for the preparation of amorphous lumacaftor, lumacaftor solvates, and an amorphous solid dispersion of lumacaftor are also disclosed.

Preparation of pharmaceutical dosage forms is often procedurally complex, particularly when combining the active ingredient with excipients. For example, workability or stability issues may arise when different components of the pharmaceutical dosage form come into intimate contact with one another. Thus, it may be advantageous to supply the manufacturer of pharmaceutical dosage forms with a pre-combined mixture of excipients and active pharmaceutical ingredient (API) to facilitate and simplify the final processing of dosages forms. The solid dispersions disclosed herein provide such pre-combined mixtures of excipients and the API.

SUMMARY OF THE INVENTION

In one aspect, the present invention provides amorphous lumacaftor.

In another aspect, the present invention provides a process for the preparation of amorphous lumacaftor.

In one embodiment, amorphous lumacaftor can be prepared by a process that includes the following steps:
 a) dissolving lumacaftor in a solvent;
 b) removing the solvent; and
 c) isolating the amorphous lumacaftor.

Within the context of this embodiment, the solvent used to dissolve the lumacaftor may be, for example, an alcohol solvent, an ester solvent, an ether solvent, a ketone solvent, a hydrocarbon solvent, an aprotic polar solvent, or mixtures thereof.

Examples of suitable alcohol solvents include, but are not limited to, methanol, ethanol, isopropanol, 1-propanol, n-butanol, 2-butanol, isobutanol, t-butanol, 2-methoxy ethanol, 2-ethoxy ethanol, and mixtures thereof. Examples of suitable ester solvents include, but are not limited to, ethyl acetate, n-propyl acetate, isopropyl acetate, n-butyl acetate, and mixtures thereof. Examples of suitable ether solvents include, but are not limited to, anisole, 1,2-dimethoxyethane, and mixtures thereof. Examples of suitable ketone solvents include, but are not limited to, methyl ethyl ketone (MEK), methyl isobutyl ketone (MIBK), and mixtures thereof. Examples of suitable hydrocarbon solvents include, but are not limited to, heptane, hexane, and mixtures thereof. Examples of suitable aprotic polar solvents include, but are not limited to, N,N-dimethylformamide (DMF), dimethylsulfoxide (DMSO), N,N-dimethylacetamide (DMA), and mixtures thereof.

In another aspect, the present invention provides an amorphous solid dispersion of lumacaftor comprising lumacaftor and a pharmaceutically acceptable excipient.

Within the context of the invention, the pharmaceutically acceptable excipient may be, for example, a polysaccharide, polyvinylpyrrolidone, polyvinyl acetate (PVAC), polyvinyl alcohol (PVA), a polymer of acrylic acid or any salt thereof, a polyacrylamide, a polymethacrylate, a vinylpyrrolidone-vinyl acetate copolymer, a $C_1$-$C_6$ polyalkylene glycol, a copolymer of polyethylene glycol and polypropylene glycol, microcrystalline cellulose, hydroxypropyl methylcellulose (HPMC), croscarmellose, carboxymethyl cellulose (CMC), methyl cellulose, hydroxyethyl cellulose, ethyl hydroxyethyl cellulose, hydroxypropyl cellulose (HPC), an optionally substituted α-cyclodextrin, an optionally substituted β-cyclodextrin, an optionally substituted γ-cyclodextrin, or mixtures thereof.

In some particularly useful embodiments, povidone K-30 or Plasdone S-630 is used as the pharmaceutically acceptable excipient.

In another aspect, the present invention provides a process for the preparation of an amorphous solid dispersion of lumacaftor which may include the following steps:
 a) forming a mixture of lumacaftor and pharmaceutically acceptable excipient in a solvent; and
 b) removing the solvent to isolate the amorphous solid dispersion of lumacaftor.

Within the context of the invention, the pharmaceutically acceptable excipient may be, for example, a polysaccharide, polyvinylpyrrolidone, polyvinyl acetate (PVAC), polyvinyl alcohol (PVA), a polymer of acrylic acid or any salt thereof, a polyacrylamide, a polymethacrylate, a vinylpyrrolidone-vinyl acetate copolymer, a $C_1$-$C_6$ polyalkylene glycol, a copolymer of polyethylene glycol and polypropylene glycol, microcrystalline cellulose, hydroxypropyl methylcellulose (HPMC), croscarmellose, carboxymethyl cellulose (CMC), methyl cellulose, hydroxyethyl cellulose, ethyl hydroxyethyl cellulose, hydroxypropyl cellulose (HPC), an optionally substituted α-cyclodextrin, an optionally substituted β-cyclodextrin, an optionally substituted γ-cyclodextrin, or mixtures thereof.

In some particularly useful embodiments, povidone K-30 or Plasdone S-630 is used as the pharmaceutically acceptable excipient.

Within the context of this embodiment, the solvent used to form the mixture of lumacaftor and pharmaceutically acceptable excipient may be an alcohol solvent, an ester solvent, an ether solvent, a ketone solvent, a hydrocarbon solvent, a chlorinated solvent, an aprotic polar solvent, or any mixtures thereof.

Examples of suitable alcohol solvents include, but are not limited to, methanol, ethanol, propanol, isopropanol, n-butanol, 2-butanol, t-butanol, 1-pentanol, 2-pentanol, 3-pentanol, 2-methyl-1-butanol, 2-methyl-2-butanol 3-methyl-2-butanol, ethylene glycol, 2,2-dimethyl-1-propanol, 2,2-dimethyl-1-butanol, and mixtures thereof. Examples of suitable ester solvents include, but are not limited to, ethyl acetate, n-propyl acetate, isopropyl acetate, n-butyl acetate. Examples of suitable ether solvents include, but are not limited to, anisole, 1,2-dimethoxyethane, and mixtures thereof. Examples of suitable ketone solvents include, but are not limited to, acetone, methyl ethyl ketone (MEK), methyl isobutyl ketone (MIBK), and mixtures thereof. Examples of suitable chlorinated solvents include, but are not limited to, dichloromethane, 1,2-dichloroethane, and mixtures thereof. Examples of suitable hydrocarbon solvents include, but are not limited to, heptane, hexane, and mixtures thereof. Examples of suitable aprotic polar solvents include, but are not limited to, N,N-dimethylformamide (DMF), dimethylsulfoxide (DMSO), N,N-dimethylacetamide (DMA), and mixtures thereof.

In another aspect, the present invention provides a crystalline lumacaftor acetic acid solvate.

Within the context of the present invention, the crystalline lumacaftor acetic acid solvate as prepared by methods disclosed herein may be characterized by a $^1$H NMR (300 MHz, DMSO-d6) spectrum having peaks at 8.99, 7.97-7.89, 7.73-7.70, 7.69-7.67, 7.57-7.52, 7.38-7.34, 7.33-7.30, 2.22, 1.91, 1.52-1.48, and 1.16-1.13.

In another aspect, the present invention provides a process for the preparation of a crystalline lumacaftor acetic acid solvate.

In one embodiment, the crystalline lumacaftor acetic acid solvate may be prepared by a process that includes the following steps:
 a) suspending lumacaftor in acetic acid solvent; and
 b) isolating the crystalline lumacaftor acetic acid solvate.

In one embodiment, the crystalline lumacaftor acetic acid solvate may be prepared by a process that includes the following steps:
 a) dissolving lumacaftor in acetic acid solvent to form a solution
 b) cooling the solution; and
 c) isolating crystalline lumacaftor acetic acid solvate.

In another aspect, the present invention provides a crystalline lumacaftor ethyl acetate solvate.

Within the context of the present invention, the crystalline lumacaftor ethyl acetate solvate as prepared by methods disclosed herein may be characterized by a $^1$H NMR (300 MHz, DMSO-d6) spectrum having peaks at 9.03, 7.98-7.89, 7.75-7.70, 7.58-7.53, 7.40-7.36, 7.35-7.32, 4.06-3.99, 2.23, 1.99, 1.53-1.49, 1.20-1.17, and 1.16-1.14.

In another aspect, the present invention provides a process for the preparation of a crystalline lumacaftor ethyl acetate solvate.

In one embodiment, the crystalline lumacaftor ethyl acetate solvate may be prepared by a process that includes the following steps:
 a) dissolving lumacaftor in ethyl acetate solvent to form a solution;
 b) optionally adding an organic solvent;
 c) cooling the solution; and
 d) isolating the crystalline lumacaftor ethyl acetate solvate.

Within the context of this embodiment, the organic solvent optionally added to the solution of lumacaftor and ethyl acetate may be a hydrocarbon solvent, for example, heptane.

When prepared by methods disclosed herein, the amorphous lumacaftor, the crystalline lumacaftor acetic acid solvate, and the crystalline lumacaftor ethyl acetate solvate may have a purity of at least 99% as measured by HPLC.

BRIEF DESCRIPTION OF THE DRAWINGS

Further aspects of the present disclosure together with additional features contributing thereto and advantages accruing therefrom will be apparent from the following description of embodiments of the disclosure which are shown in the accompanying figures wherein.

DETAILED DESCRIPTION OF THE INVENTION

Figure 1:
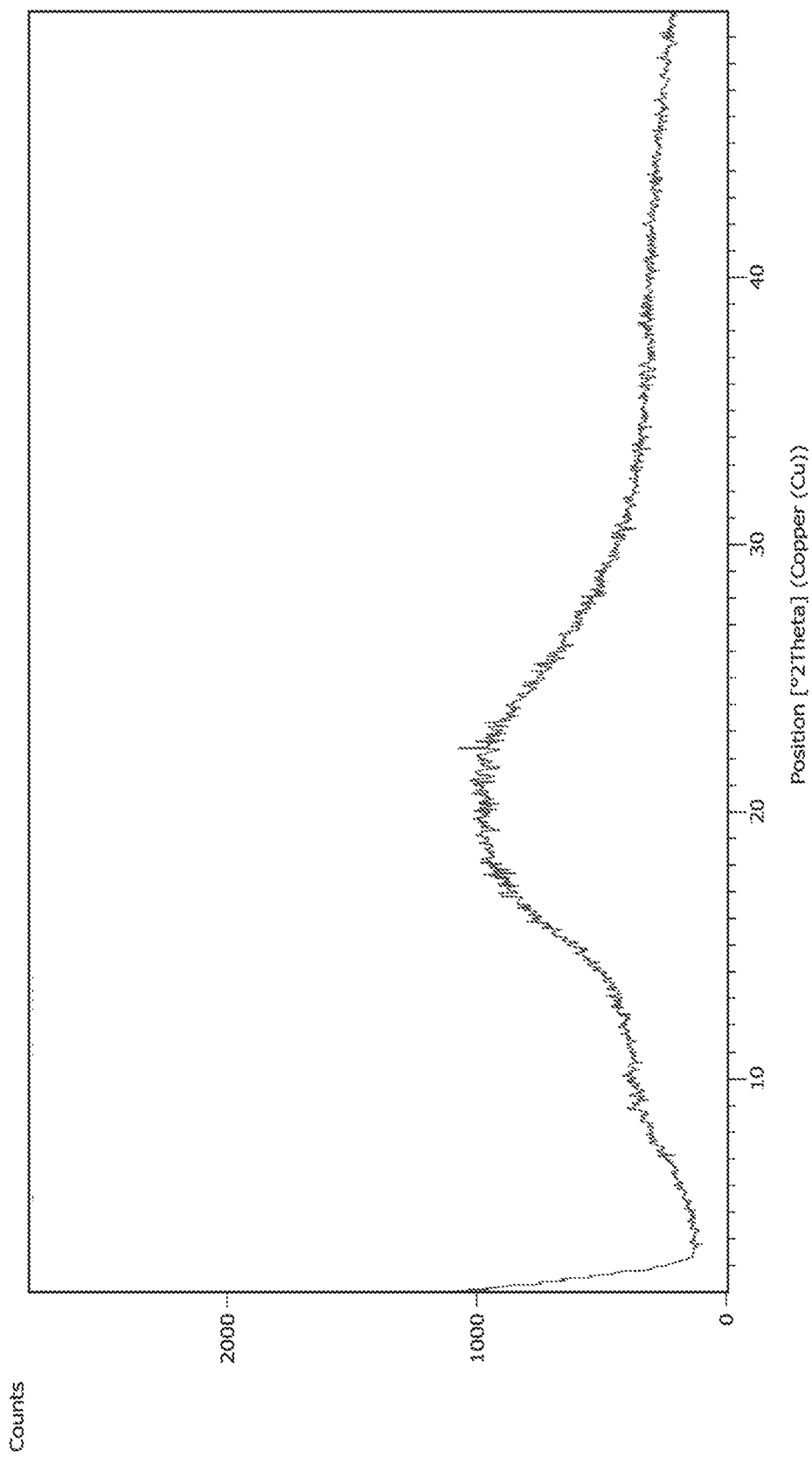
FIG. 1 shows a powder X-ray diffraction (PXRD) pattern of amorphous lumacaftor.

One aspect of the present invention provides a process for the preparation of amorphous lumacaftor.

In one embodiment, amorphous lumacaftor may be prepared by a method including the following steps:
  a) dissolving lumacaftor in a solvent; and
  b) removing the solvent to isolate amorphous lumacaftor.

According to this embodiment, lumacaftor may first be dissolved in a solvent. The solvent useful for this embodiment may be, for example, an alcohol solvent, an ester solvent, an ether solvent, a ketone solvent, a hydrocarbon solvent, an aprotic polar solvent, or mixtures thereof.

Within the context of the present embodiment, the starting lumacaftor material may be in any form, such as a crystalline form of lumacaftor or a solvated form of lumacaftor.

Examples of suitable alcohol solvents include, but are not limited to, methanol, ethanol, isopropanol, 1-propanol, n-butanol, 2-butanol, isobutanol, t-butanol, 2-methoxy ethanol, 2-ethoxy ethanol, and mixtures thereof. Examples of suitable ester solvents include, but are not limited to, ethyl acetate, n-propyl acetate, isopropyl acetate, n-butyl acetate, and mixtures thereof. Examples of suitable ether solvents include, but are not limited to, anisole, 1,2-dimethoxyethane, and mixtures thereof. Examples of suitable ketone solvents include, but are not limited to, acetone, methyl ethyl ketone (MEK), methyl isobutyl ketone (MIBK), and mixtures thereof. Examples of suitable hydrocarbon solvents include, but are not limited to, heptane, hexane, and mixtures thereof. Examples of suitable aprotic polar solvents include, but are not limited to, N,N-dimethylformamide (DMF), dimethylsulfoxide (DMSO), N,N-dimethylacetamide (DMA), and mixtures thereof. In some particularly useful embodiments, methanol is used as the solvent.

In some embodiments, depending on the solvent used, it is useful to dissolve lumacaftor in the solvent at an elevated temperature. One of skill in the art will be able to determine the appropriate solvent and temperature conditions needed to dissolve lumacaftor in a solvent without undue experimentation. For example, in some particularly useful embodiments, lumacaftor is dissolved in methanol at about 60° C. to about 65° C.

Next, the solvent may be removed to isolate amorphous lumacaftor as a solid. This may be carried out by conventional methods well-known in the art. For example, the solvent may be removed by distillation, spray drying, agitated thin film drying or freeze drying. In some embodiments, it is found to be particularly useful to remove the solvent by spray drying.

In another aspect, an embodiment of the present invention provides amorphous lumacaftor.

Amorphous lumacaftor as prepared by methods herein may be characterized as amorphous by powder X-ray diffraction (PXRD). Thus, samples of amorphous lumacaftor were analyzed by X-ray diffraction on a BRUKER D-8 Discover powder diffractometer equipped with a goniometer of θ/2θ configuration and Lynx Eye detector. The Cu-anode X-ray tube was operated at 40 kV and 30 mA. The experiments were conducted over the 2θ range of 2.0°-50.0°, 0.030° step size, and 0.4 seconds step time.

Within the context of this embodiment, amorphous lumacaftor, prepared by the methods disclosed herein, may be characterized as amorphous by the PXRD pattern in FIG. 1.

The purity of amorphous lumacaftor, prepared by methods disclosed herein may be analyzed by HPLC. Therefore, samples of amorphous lumacaftor was analyzed by HPLC.

Thus, in addition to PXRD analyses, HPLC analyses were also performed. HPLC separations may be performed on an HPLC column and detector system, such as an Kromasil 100 C18 column (150×4.6 mm, 3.5 μm) or its equivalent using a UV detector set at 220 nm with a column oven temperature of about 30° C. A flow rate of 1.0 mL/min with an injection volume of 10 μL may be used, with a run time of approximately 35 minutes.

In some embodiments, amorphous lumacaftor prepared according to processes disclosed herein may have a purity of 99% or more, as measured by HPLC.

Another aspect of the present invention provides a process for the preparation of an amorphous solid dispersion of lumacaftor.

In one embodiment, an amorphous solid dispersion of lumacaftor may be prepared by methods including the following steps:
  a) preparing a solution of lumacaftor and a pharmaceutically acceptable excipient in a solvent; and
  b) removing the solvent to isolate the amorphous solid dispersion of lumacaftor.

According to this embodiment, a solution of lumacaftor and a pharmaceutically acceptable excipient is first formed. In some embodiments, this step may be carried out by adding lumacaftor and the pharmaceutically acceptable excipient to a solvent at the same time. In other embodiments, it may be carried out by first dissolving lumacaftor in a solvent and then adding the pharmaceutically acceptable excipient to the solution. In yet other embodiments, the pharmaceutically acceptable excipient may be added to a solvent and lumacaftor may be added to that solution. Depending on the solubility of the pharmaceutically acceptable excipient, the resulting mixture of lumacaftor and the pharmaceutically acceptable excipient in the solvent may be a solution (wherein both lumacaftor and the pharmaceutically acceptable excipient are dissolved) or it may be a suspension (wherein either or both of the lumacaftor and the pharmaceutically acceptable excipient are partially dissolved or not dissolved at all).

Within the context of the present embodiment, the starting lumacaftor material may be in any form, such as a crystalline form of lumacaftor or a solvated form of lumacaftor.

Examples of suitable solvents include, but are not limited to, alcohol solvents, ester solvents, ether solvents, ketone solvents, chlorinated solvents, hydrocarbon solvents, aprotic polar solvents, and mixtures thereof.

Examples of suitable alcohol solvents include, but are not limited to, methanol, ethanol, propanol, isopropanol, n-butanol, 2-butanol, t-butanol, 1-pentanol, 2-pentanol, 3-pentanol, 2-methyl-1-butanol, 2,2-dimethyl-1-butanol, 3-methyl-2-butanol, ethylene glycol, 2,2-dimethyl-1-propanol, 2-methyl-2-butanol, and mixtures thereof. Examples of suitable ester solvents include, but are not limited to, ethyl acetate, n-propyl acetate, isopropyl acetate, n-butyl acetate, and mixtures thereof. Examples of suitable ether solvents include, but are not limited to, anisole, 1,2-dimethoxyethane, and mixtures thereof. Examples of suitable ketone solvents include, but are not limited to, acetone, methyl ethyl ketone (MEK), methyl isobutyl ketone (MIBK), and mixtures thereof. Examples of suitable chlorinated solvents include, but are not limited to, dichloromethane, 1,2-dichloroethane, and mixtures thereof. Examples of suitable hydrocarbon solvents include, but are not limited to, heptane, hexane, and mixtures thereof. Examples of suitable aprotic polar solvents include, but are not limited to, N,N-dimethylformamide (DMF), dimethylsulfoxide (DMSO), N,N-dimethylacetamide (DMA), and mixtures thereof. In some embodiments, the use of ethanol as a solvent is found to be particularly useful.

Next, a pharmaceutically acceptable excipient may be added to the solution. Within the context of this embodiment, the pharmaceutically acceptable excipient encompasses one or more pharmaceutically acceptable excipients. Within the context of this embodiment, the pharmaceutically acceptable excipient may be combined with the lumacaftor solution either as a solid or as a solution in which the pharmaceutically acceptable excipient or excipients are dissolved. If the pharmaceutically acceptable excipient or excipients are added to the lumacaftor solution in the form of a solution, the solvent used to dissolve the pharmaceutically acceptable excipient may be different or the same as the solvent used to dissolve the lumacaftor.

Examples of suitable pharmaceutical excipients include, but are not limited to, polysaccharides, polyvinylpyrrolidone (povidone), polyvinyl acetate (PVAC), polyvinyl alcohol (PVA), polymers of acrylic acid and their salts, polyacrylamide, polymethacrylates, vinylpyrrolidone-vinyl acetate copolymers, $C_1$-$C_6$ polyalkylene glycols (e.g., polypropylene glycol, polyethylene glycol), copolymers of polyethylene glycol and polypropylene glycol (e.g., the families of block copolymers based on ethylene oxide and propylene oxide sold under the PLURONIC® tradename), and mixtures thereof. Suitable polysaccharides include, for example, microcrystalline cellulose, hydroxypropyl methylcellulose (HPMC), croscarmellose, carboxymethyl cellulose (CMC) and salts thereof, methylcellulose, hydroxyethyl cellulose, ethyl hydroxyethyl cellulose, hydroxypropyl cellulose (HPC), optionally substituted α-cyclodextrins, optionally substituted β-cyclodextrins (e.g., hydroxypropyl β-cyclodextrin), optionally substituted γ-cyclodextrins (e.g., hydroxypropyl γ-cyclodextrin), and mixtures thereof. As used herein, the term "substituted" with respect to cyclodextrins means the addition of side chain groups, for example, hydroxyl, hydroxypropyl, $C_1$-$C_6$ alkyl, and other $C_1$-$C_6$ hydroxyalkyl.

Within the context of this embodiment, polyvinylpyrrolidone with K-values ranging from about 12 to about 103 may be particularly useful, including povidone K-12, povidone K-15, povidone K-17, povidone K-25, povidone K-30, povidone K-90, and mixtures thereof. One of skill in the art would readily recognize different forms of polyvinylpyrrolidone/povidone that would be useful and how each form may confer desired properties to the final dosage form. As used herein, "about" means plus or minus 10% of the recited value.

In some embodiments, it is found that adding a vinylpyrrolidone-vinyl acetate copolymer, polyvinylpyrrolidone, or a cyclodextrin (e.g., an optionally substituted α-cyclodextrin, an optionally substituted β-cyclodextrin, or an optionally substituted γ-cyclodextrin) to the solution of lumacaftor is particularly useful.

In other particularly useful embodiments, a copolymer of N-vinyl-2-pyrrolidone and vinyl acetate is utilized as a pharmaceutically acceptable excipient. One example of a suitable N-vinyl-2-pyrrolidone/vinyl acetate copolymer is a copolymer of N-vinyl-2-pyrrolidone and vinyl acetate with a mass ratio of 60:40 (e.g., PLASDONE S-630 or KOLLIDON® VA 64).

In other embodiments, polyvinylpyrrolidone (often also referred to as "povidone") was found to be particularly useful as a pharmaceutically acceptable excipient. Polyvinylpyrrolidone with a K-value of about 30 and an average molecular weight of 40 kDa (e.g., povidone K-30) was found to be particularly useful as a pharmaceutically acceptable excipient. In yet other particularly useful embodiments, Plasdone S-630 or povidone K-30 may be employed as a pharmaceutically acceptable excipient.

As used herein, the term "molecular weight" means the weight-average molecular weight (MW).

Within the context of this embodiment of the present disclosure, the pharmaceutically acceptable excipient may be combined with the solution of lumacaftor in an amount from about 1% w/w (pharmaceutically acceptable excipient/total final composition mass) to about 80% w/w, which may be about 1% w/w, 2% w/w, 5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w or between any of the aforementioned w/w percentages, including the ranges of about 10%-40%, 10%-30%, 10%-20%, 20%-50%, 20%-40%, 20-30%, 30%-50%, 30%-400/%, and 40%-50% w/w. In some embodiments of the present invention, combining a vinylpyrrolidone-vinyl acetate copolymer (e.g., a copolymer with a 40:60 ratio of N-vinyl-2-pyrrolidone to vinyl acetate) at concentrations recited above, including from about 10% to 50% w/w, with lumacaftor was found to be useful. In other embodiments of the present disclosure, combining polyvinylpyrrolidone (e.g., a polyvinylpyrrolidone with a K-value of 30) with lumacaftor at concentrations recited above, including from about 10% to 50% w/w, was found to be useful. Within the context of the present invention, final composition mass refers to the mass of the amorphous solid dispersion after solvent is removed.

Next, the solvent may be removed from the solution to isolate an amorphous solid dispersion of lumacaftor and the pharmaceutically acceptable excipient. Solvent removal may be carried out by techniques well known in the art, such as evaporation, distillation, spray drying, lyophilization, agitated thin film drying, or combinations thereof. In certain embodiments of the present disclosure, the technique of spray drying is particularly useful for removing the solvent.

Figure 2:
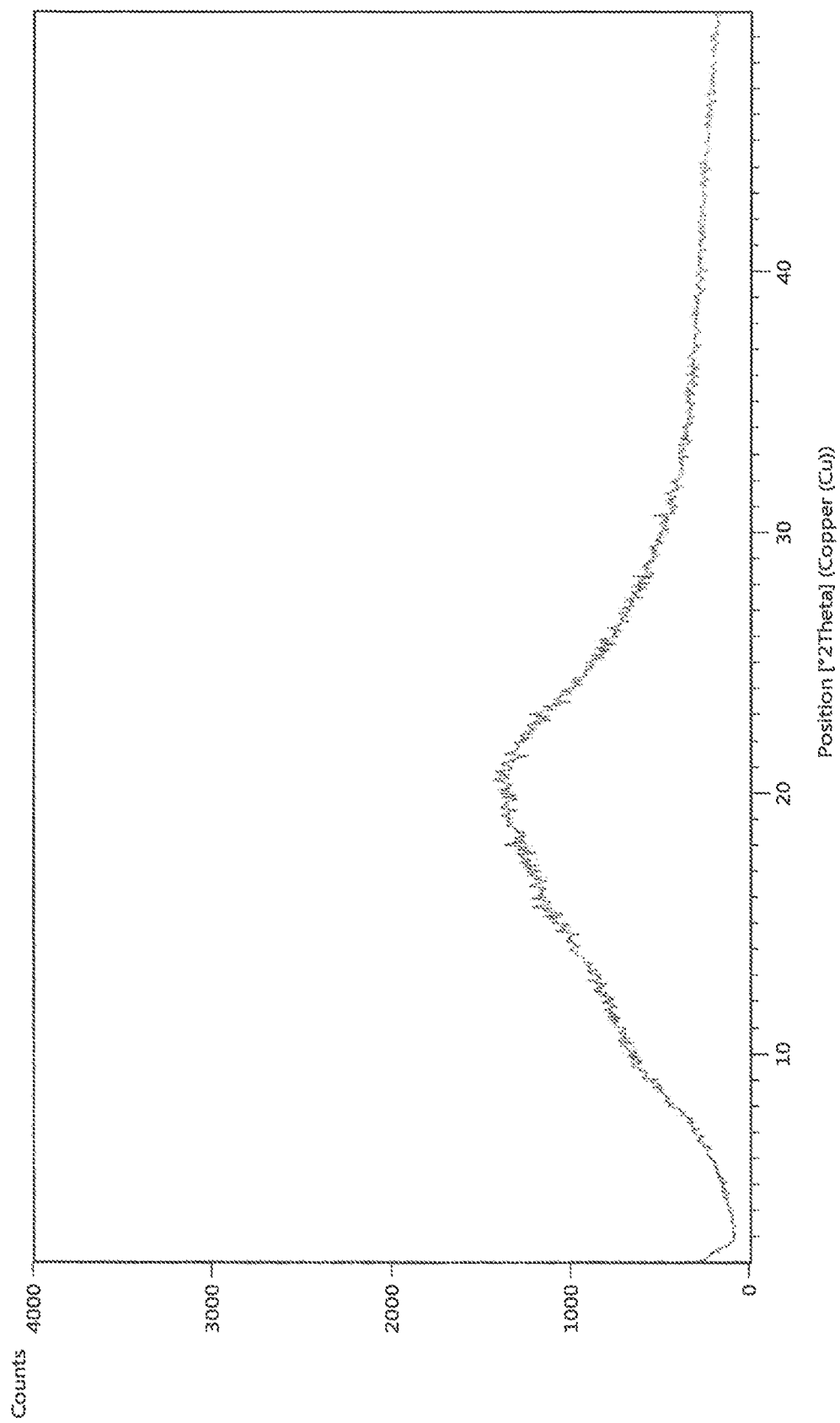
FIG. 2 shows a PXRD pattern of an amorphous solid dispersion of lumacaftor.

Within the context of this embodiment, the amorphous solid dispersion of lumacaftor may be characterized by the PXRD pattern shown in FIG. 2.

Another aspect of the present invention provides a process for the preparation of a lumacaftor acetic acid solvate.

In one embodiment, the lumacaftor acetic acid solvate may be prepared by a method that includes the following steps:

a) suspending lumacaftor in acetic acid to prepare a suspension; and b) isolating lumacaftor acetic acid solvate.

According to this embodiment, lumacaftor is suspended in acetic acid. In some embodiments, the acetic acid is in the form of a concentrated solution of acetic acid. For example, a concentration greater than about 95% is found to be particularly useful.

Within the context of the present embodiment, the starting lumacaftor material may be in any form, such as a crystalline form of lumacaftor or amorphous lumacaftor.

In some embodiments, it is found useful to stir or agitate the suspension. In such embodiments, the stirring or agitation may be carried out at a temperature of about 15° C. to about 40° C. In some embodiments, a temperature of about 25° C. to about 30° C. is used. In some embodiments, the stirring or agitation may be carried out for about 2 hours to about 5 days. In some particularly useful embodiments, agitation or stirring the solution is carried out for 3 days. Next, lumacaftor acetic acid solvate may be isolated. This may be carried out by methods well-known in the art. For example, the suspension may be filtered to isolate solid crystalline lumacaftor acetic acid solvate.

In another embodiment, lumacaftor acetic acid solvate may be prepared by a method that includes by the following steps:
 a) dissolving lumacaftor in acetic acid to form a solution;
 b) cooling the solution; and
 c) isolating crystalline lumacaftor acetic acid solvate.

According to this embodiment, lumacaftor is dissolved in acetic acid. Dissolving lumacaftor in acetic acid may be facilitated by using an elevated temperature. For example, a temperature of about 55° C. to about 95° C. may be used. In some embodiments, about 70° C. to about 80° C. is used. In some embodiments, the acetic acid is in the form of a concentrated solution of acetic acid. For example, a concentration greater than about 95% is found to be particularly useful.

Within the context of the present embodiment, the starting lumacaftor material may be in any form, such as a crystalline form of lumacaftor or a solvated form of lumacaftor.

Next, the solution may be cooled. In some embodiments, it is found to be useful to cool the solution to 15° C. to about 35° C. In particular embodiments, the solution is cooled to a temperature of about 20° C. to about 30° C. In some embodiments, it is found useful to stir the solution for about 2 to about 4 days. In particularly useful embodiments, the solution is stirred for 2 days. In some embodiments, cooling and stirring the solution will cause a solid of crystalline lumacaftor acetic acid solvate to form.

Next, lumacaftor acetic acid solvate may be isolated. This may be carried out by methods well-known in the art. For example, the solution may be filtered to isolate solid crystalline lumacaftor acetic acid solvate.

Another aspect of the present invention provides a crystalline lumacaftor acetic acid solvate. The crystalline lumacaftor acetic acid solvate prepared by methods disclosed herein may be characterized by PXRD. Thus, PXRD analyses of the crystalline lumacaftor acetic acid solvate were carried out on a PANalytical, X'Pert PRO powder diffractometer equipped with goniometer of θ/θ configuration and X'Celerator detector. The Cu-anode X-ray tube was operated at 40 kV and 30 mA. The experiments were conducted over the 2θ range of 2.0°-50.0°, 0.030° step size, and 50 seconds step time.

Figure 3:
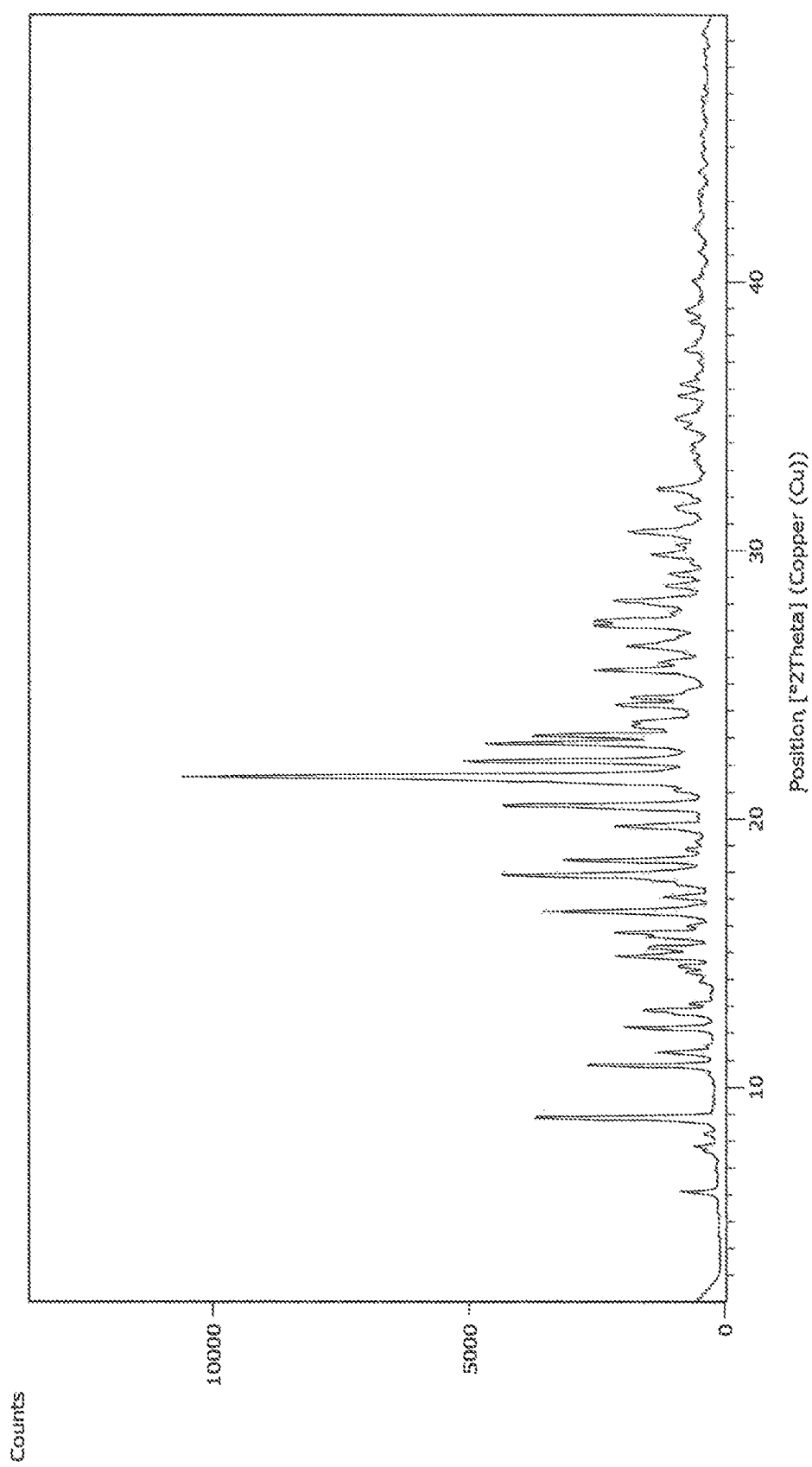
FIG. 3 shows a PXRD pattern of a lumacaftor acetic acid solvate prepared by methods disclosed herein.

Within the context of this embodiment, the crystalline lumacaftor acetic acid solvate prepared by methods disclosed herein may be characterized by the PXRD pattern in FIG. 3.

Within the context of this embodiment, the application provides the crystalline lumacaftor acetic acid solvate characterized by a PXRD pattern comprising the peaks at about 8.87, 16.53, 17.89, 20.50, 21.55, 22.13, 22.80 and 23.09±0.2° 2θ.

Within the context of this embodiment, the application provides the crystalline lumacaftor acetic acid solvate further characterized by a PXRD pattern comprising the peaks at about 8.87, 10.81, 16.53, 17.89, 18.44, 20.50, 21.55, 22.13, 22.80, 23.09, 27.15 and 27.40±0.2° 2θ.

Within the context of this embodiment, the solvates disclosed herein may also be characterized by differential scanning calorimetry (DSC). DSC measurements were carried out on a TA Q1000 DSC (TA Instruments). The experiments were performed at a heating rate of 10.0° C./min over a temperature range of 30-250° C., purging with nitrogen at a flow rate of 50 mL/min. Standard aluminum crucibles covered by lids with pin holes were used.

Figure 4:
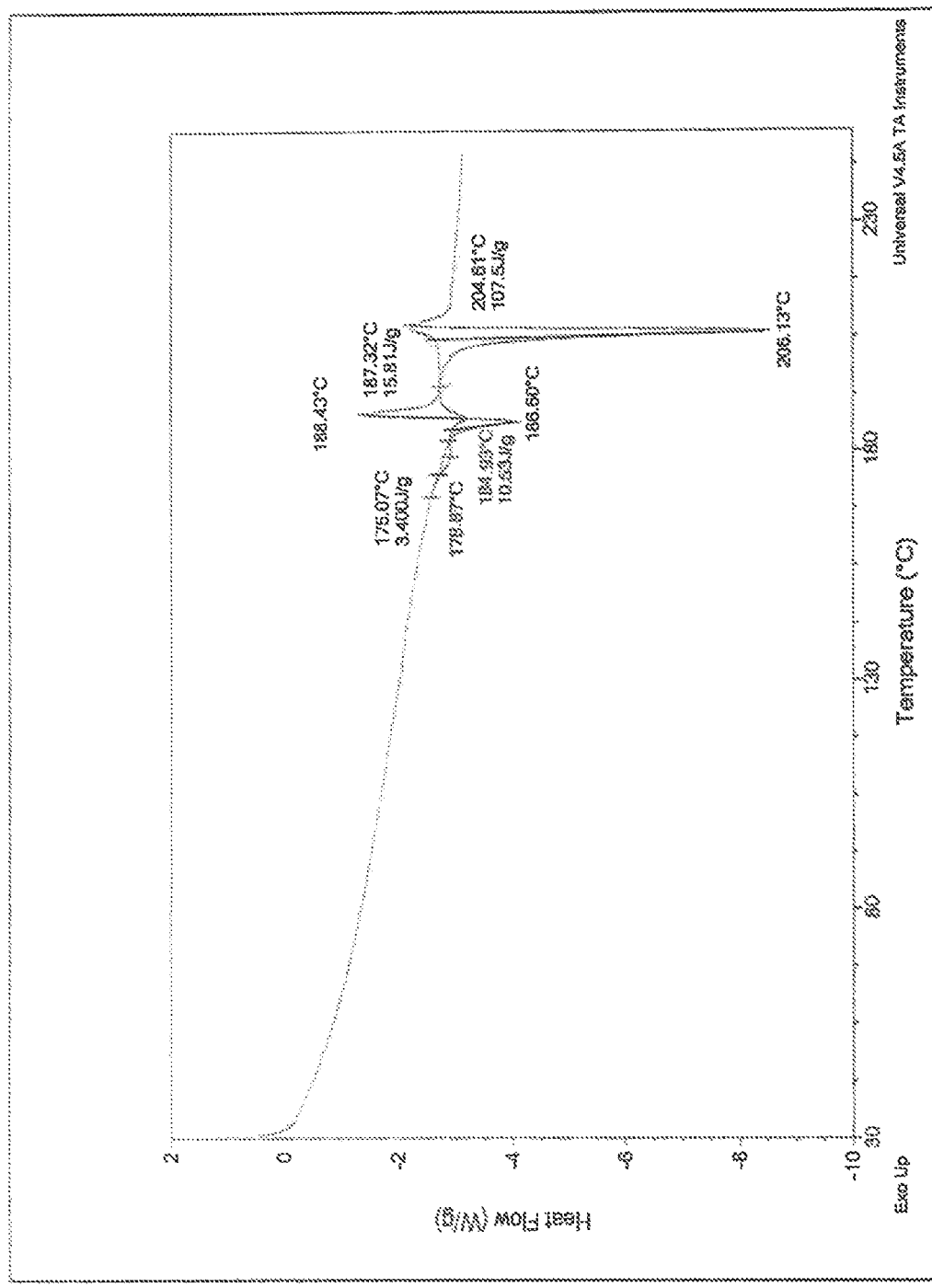
FIG. 4 shows a differential scanning calorimetry (DSC) thermogram of a lumacaftor acetic acid solvate prepared by methods disclosed herein.

Within the context of this embodiment, the crystalline lumacaftor acetic acid solvate may be characterized by the DSC thermogram in FIG. 4.

The solvates of the present invention may also be characterized by thermogravimetric analysis (TGA) or differential thermal analysis (DTA). TGA/DTA was recorded using a TA Q5000 SA (TA Instruments). The experiments were performed at a heating rate of 10.0° C./min over a temperature range of 30° C.-300° C. purging with nitrogen at a flow rate of 25 mL/min.

Figure 5:
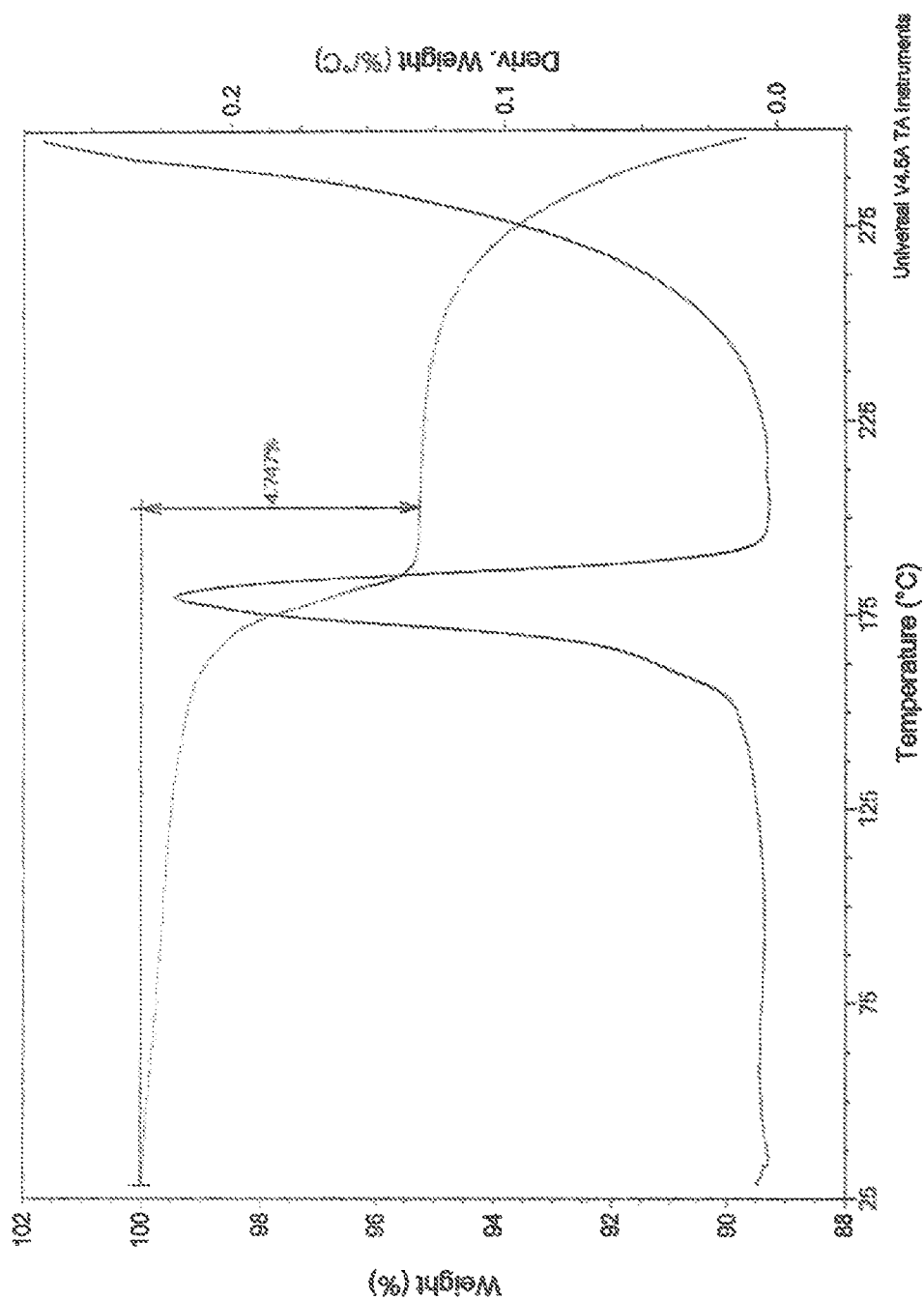
FIG. 5 shows a thermal gravimetric analysis/differential thermal analysis (TGA/DTA) thermogram of a lumacaftor acetic acid solvate prepared by methods disclosed herein.

Based on the data found in FIG. 5, it is believed that the lumacaftor acetic acid solvate has a lumacaftor:acetic acid ratio of about 1:0.2 to about 1:0.3.

Within the context of this embodiment, the crystalline lumacaftor acetic acid solvate may be characterized by the TGA/DTA thermogram in FIG. 5.

The crystalline lumacaftor acetic acid solvate disclosed herein may also be characterized by proton NMR ($^1$H NMR). $^1$H NMR experiments were performed on a Bruker 300 MHz Avance NMR spectrometer equipped with 5 mm BBO probe in DMSO-d6. Data were collected and processed by XWIN-NMR software.

Figure 6:
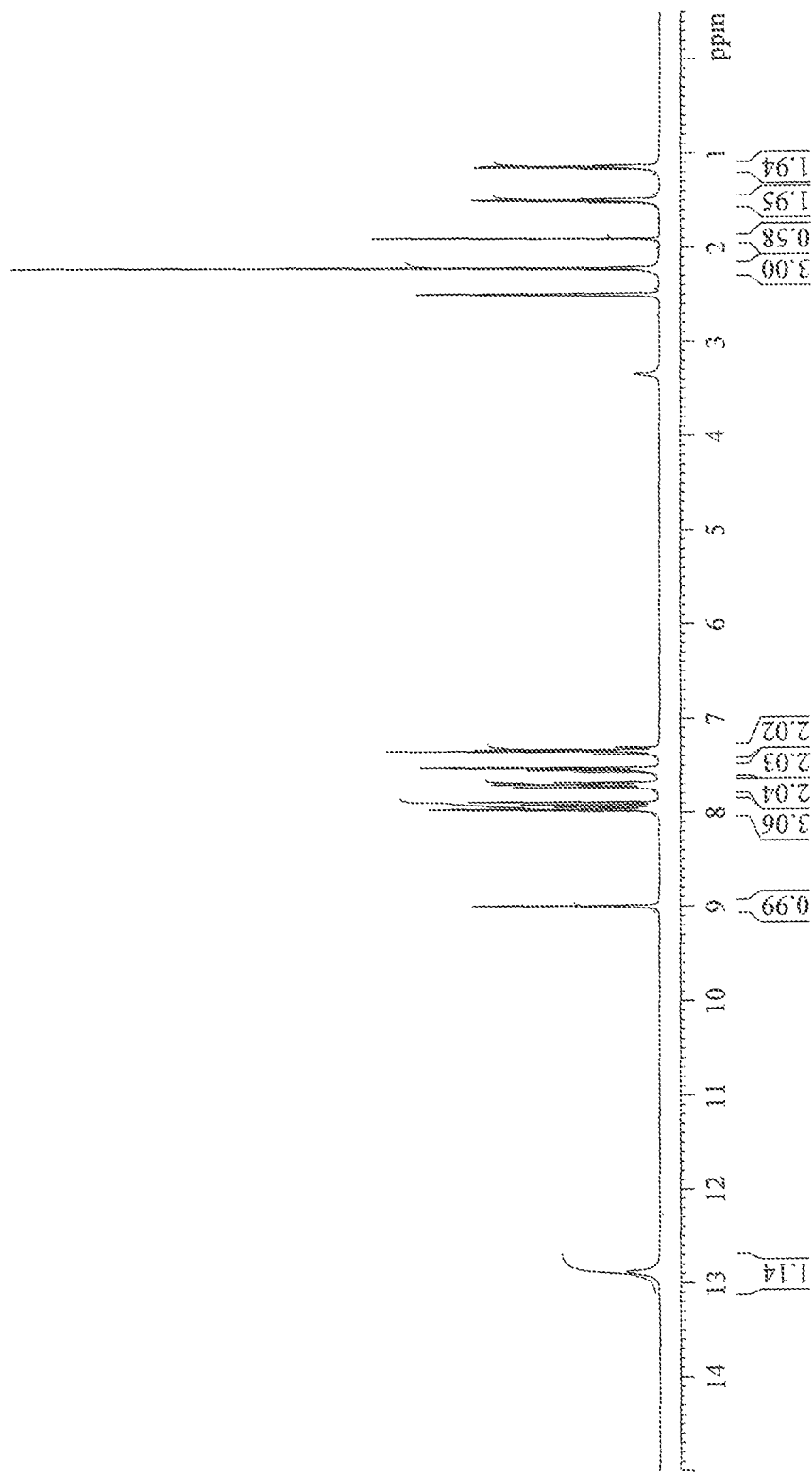
FIG. 6 shows a $^1$H NMR spectrum of a lumacaftor acetic acid solvate prepared by methods disclosed herein.

Within the context of this embodiment, the crystalline lumacaftor acetic acid solvate may be characterized by a $^1$H NMR (300 MHz, DMSO-d6) spectrum having peaks at 8.99, 7.97-7.89, 7.73-7.70, 7.69-7.67, 7.57-7.52, 7.38-7.34, 7.33-7.30, 2.22, 1.91, 1.52-1.48, and 1.16-1.13. The crystalline lumacaftor acetic acid solvate of the present invention may be further characterized by the $^1$H NMR spectrum in FIG. 6.

Another aspect of the present invention provides a process for the preparation of a crystalline lumacaftor ethyl acetate solvate. In one embodiment, crystalline lumacaftor ethyl acetate solvate may be prepared by a method including the following steps:
 a) dissolving lumacaftor in ethyl acetate;
 b) optionally adding an organic solvent;
 c) cooling the solution; and
 d) isolating crystalline lumacaftor ethyl acetate solvate.

According to this embodiment, lumacaftor is first dissolved in ethyl acetate. Next, an organic solvent may be optionally added. The organic solvent may be a hydrocarbon solvent, for example, pentane, hexane, heptane, or a mixture thereof. For example, in some embodiments, heptane is used.

According to this embodiment, the solution may next be cooled to a temperature of about 0° C. to about −20° C., resulting in formation of a solid which may be identified as crystalline lumacaftor ethyl acetate solvate. In some particularly useful embodiments, the solution is cooled to about −20° C.

Next, the crystalline lumacaftor ethyl acetate solvate may be isolated. This may be carried out by methods well-known in the art. For example, the solution and precipitate may be filtered to isolate solid crystalline lumacaftor ethyl acetate solvate.

Figure 7:
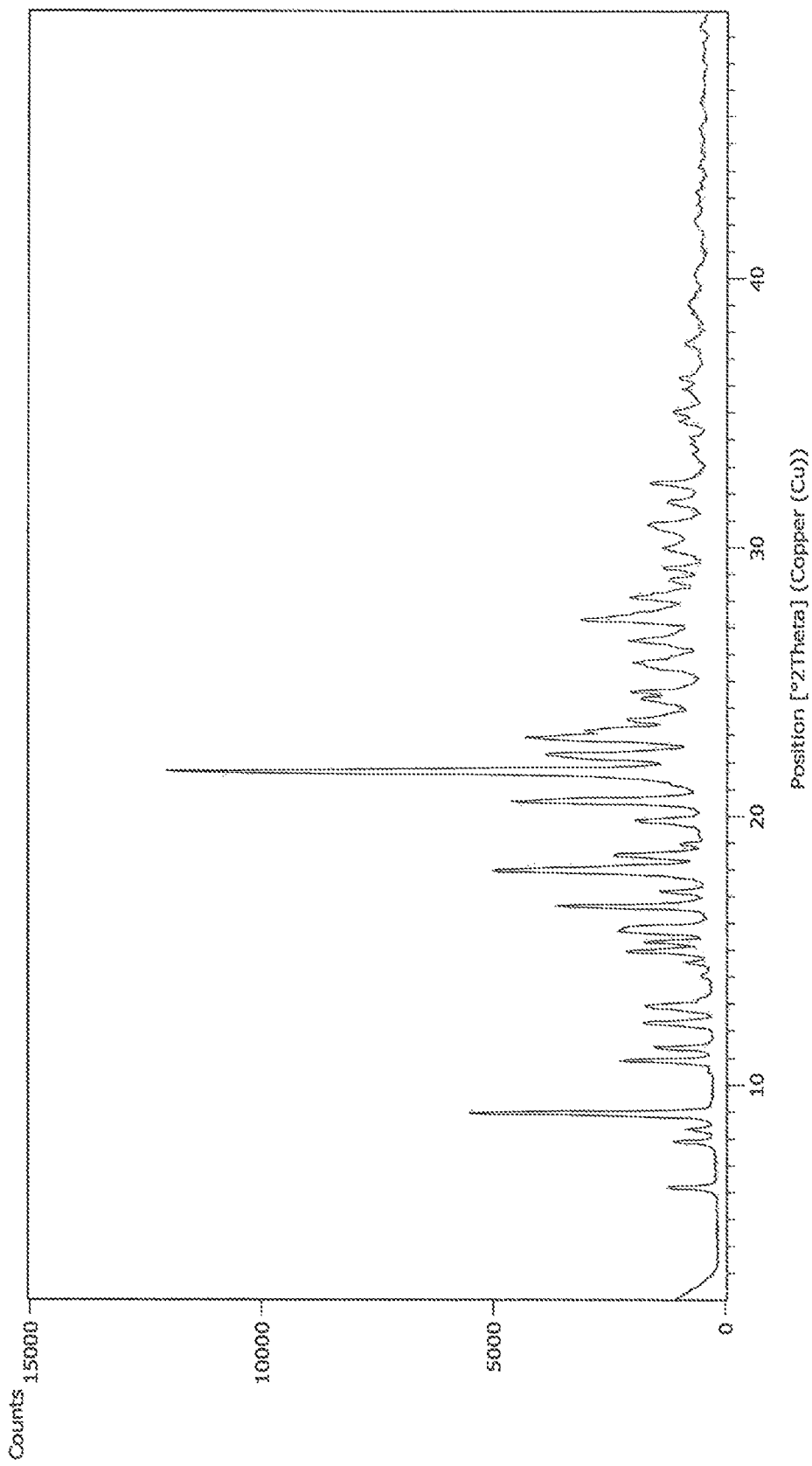
FIG. 7 shows a PXRD pattern of a lumacaftor ethyl acetate solvate as prepared by methods disclosed herein.

Another aspect of the present invention provides crystalline lumacaftor ethyl acetate solvate. According to the present embodiment, the crystalline lumacaftor ethyl acetate solvate prepared by methods disclosed herein may be characterized by the PXRD pattern in FIG. 7.

Within the context of this embodiment, the application provides the crystalline lumacaftor ethyl acetate solvate characterized by a PXRD pattern comprising the peaks at about 8.96, 17.93, 20.51, 21.65, 22.31 and 22.87±0.2° 2θ.

Within the context of this embodiment, the application provides the crystalline lumacaftor ethyl acetate solvate further characterized by a PXRD pattern comprising the peaks at about 8.96, 16.63, 17.93, 20.51, 21.65, 22.31, 22.87, 23.21 and 27.27±0.2° 2θ.

The lumacaftor ethyl acetate solvate prepared by methods disclosed herein may be characterized by PXRD. Thus, PXRD analyses of the lumacaftor ethyl acetate solvate were carried out on a PANalytical, X'Pert PRO powder diffractometer equipped with goniometer of θ/θ configuration and X'Celerator detector. The Cu-anode X-ray tube is operated at 40 kV and 30 mA. The experiments were conducted over the 2θ range of 2.0°-50.0°, 0.0300 step size, and 50 seconds step time.

Figure 8:
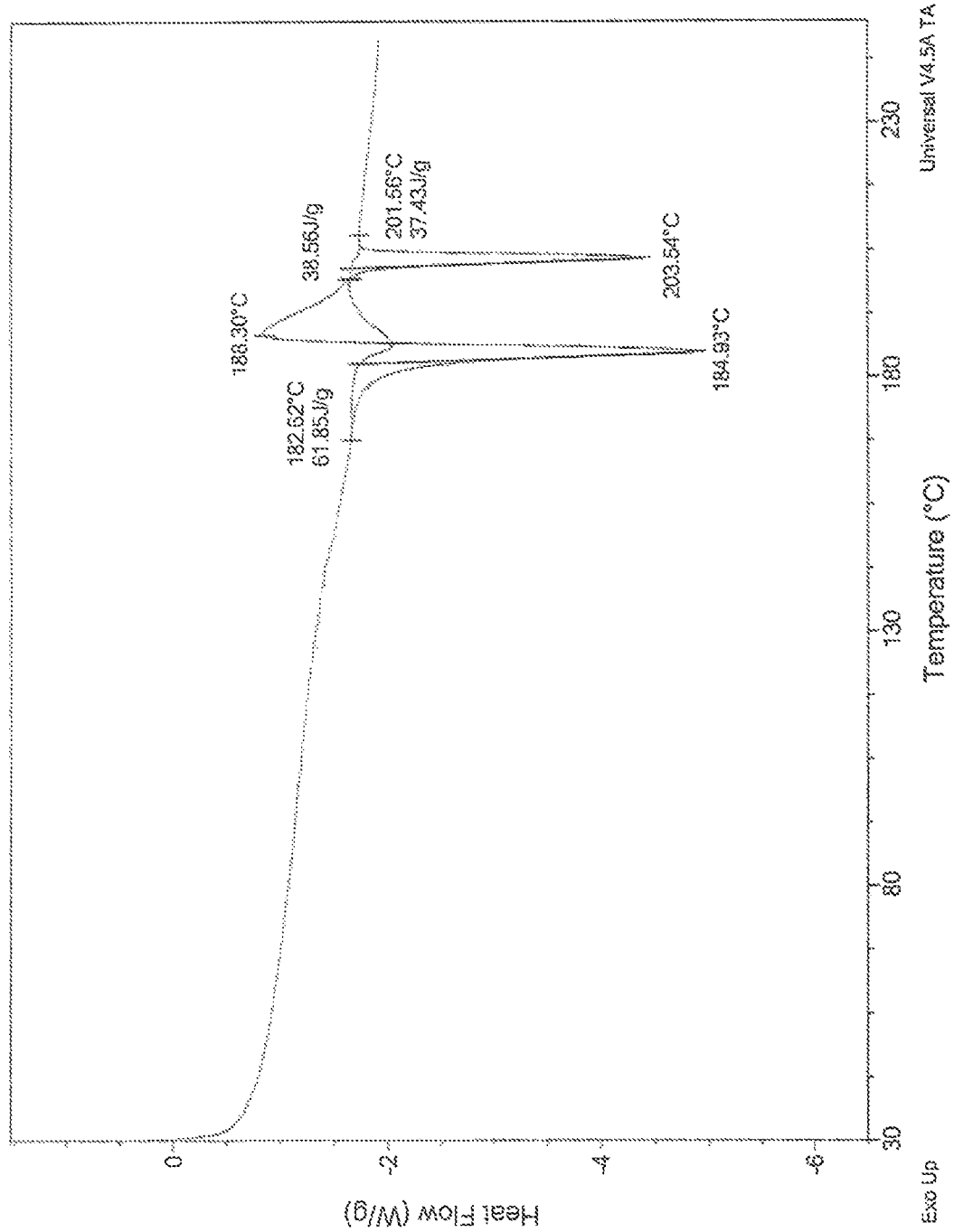
FIG. 8 shows a DSC thermogram of a lumacaftor ethyl acetate solvate as prepared by methods disclosed herein.

Within the context of this embodiment, the crystalline lumacaftor ethyl acetate solvate may be further characterized by the DSC thermogram in FIG. 8. Within the context of this embodiment, the crystalline lumacaftor ethyl acetate solvate may be further characterized by the TGA/DTA thermogram in FIG. 9.

Figure 9:
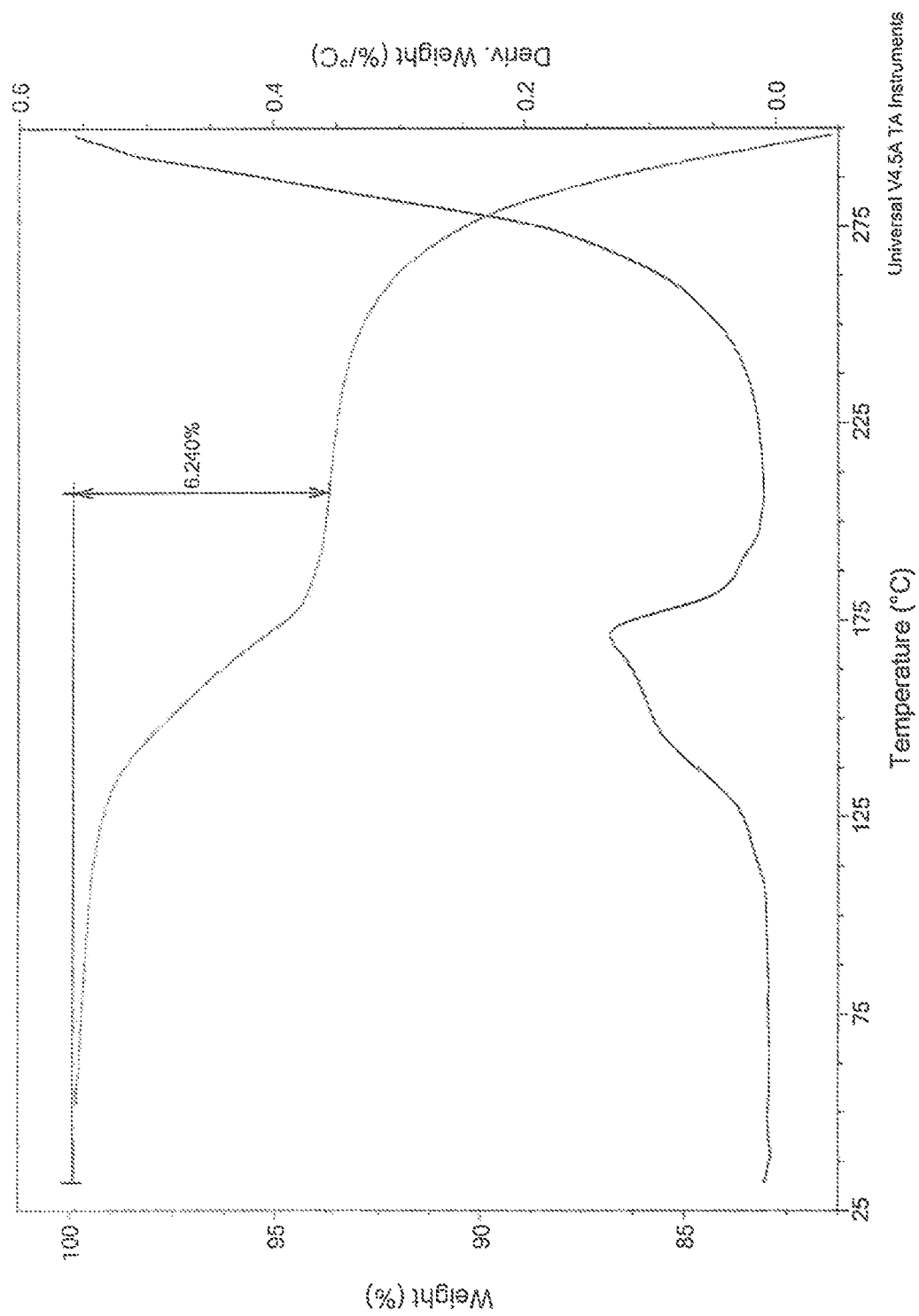
FIG. 9 shows a TGA/DTA thermogram of a lumacaftor ethyl acetate solvate as prepared by methods disclosed herein.

Based on the data found in FIG. 9, it is believed that the lumacaftor ethyl acetate solvate has a lumacaftor:ethyl acetate ratio of about 1:0.3 to about 1:0.4.

Figure 10:
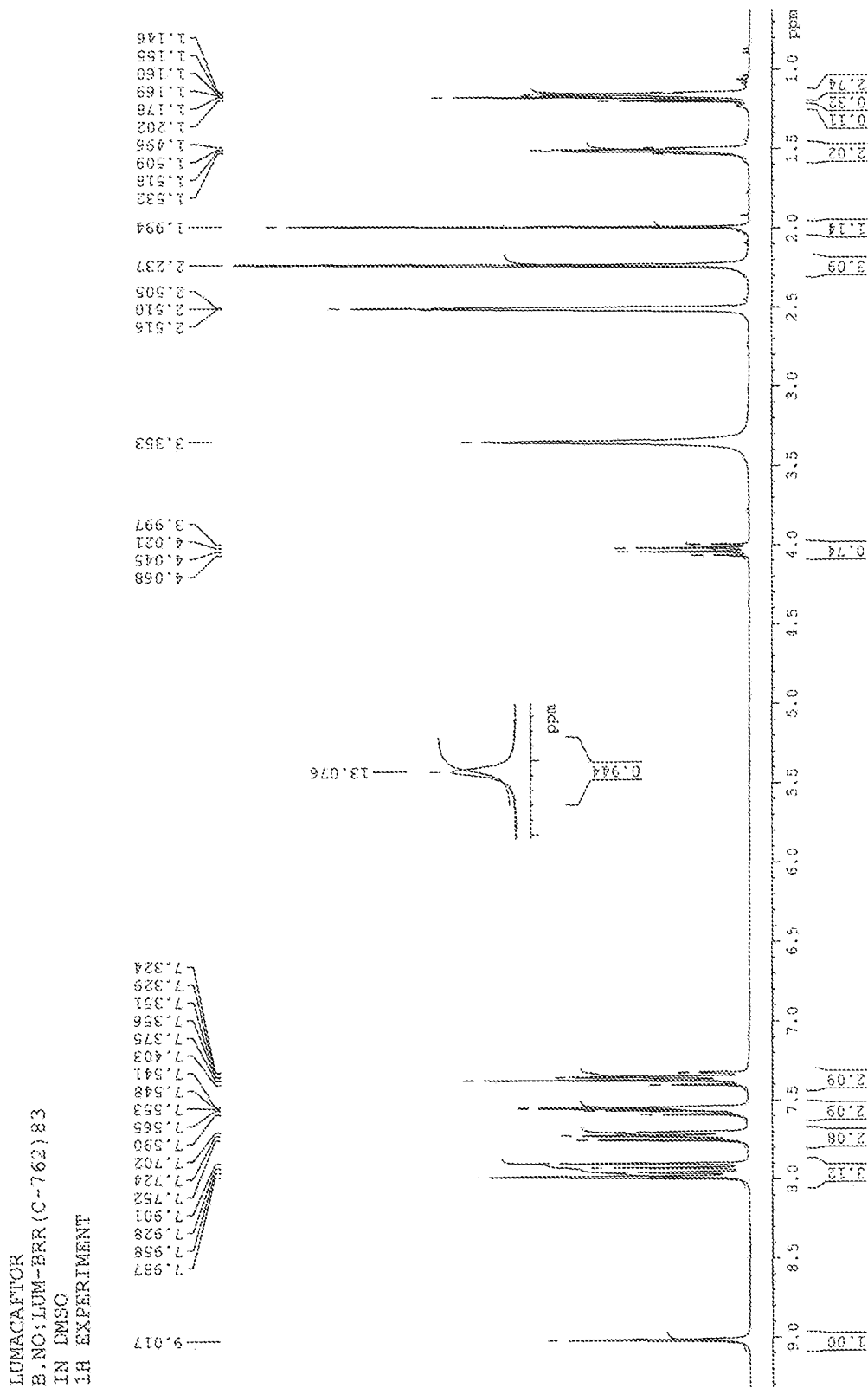
FIG. 10 shows a $^1$H NMR spectrum of a lumacaftor ethyl acetate solvate as prepared by methods disclosed herein.

Within the context of this embodiment, the crystalline lumacaftor ethyl acetate solvate may be further characterized by a $^1$H NMR spectrum having peaks at 9.03, 7.98-7.89, 7.75-7.70, 7.58-7.53, 7.40-7.36, 7.35-7.32, 4.06-3.99, 2.23, 1.99, 1.53-1.49, 1.20-1.17, and 1.16-1.14. Within the context of this embodiment, the crystalline lumacaftor ethyl acetate solvate may be further characterized by the $^1$H NMR spectrum in FIG. 10.

The crystalline lumacaftor ethyl acetate solvate prepared by methods disclosed herein may be characterized by Fourier transform infrared (FTIR) analysis. Thus, samples of crystalline lumacaftor ethyl acetate solvate were analyzed by FTIR.

Thus, in addition to $^1$H NMR spectrum analyses, FTIR analyses were also performed. FTIR spectra were recorded on Spectrum One Perkin-Elmer FTIR spectrophotometer equipped with DTGS detector. The spectra were recorded using KBr disc method in the range from 4000 cm$^{-1}$ to 400 cm$^{-1}$ with three scans per sample taking the air as reference. About 300 to 400 mg of KBr, previously dried at 200° C. and cooled was weighed, and ground to a fine powder into a mortar. About 2.0 mg of test sample is added and mixed well and ground to a fine powder. A small quantity of powder was used to make a thin semitransparent pellet. This thin pellet is then kept in sample holder which was then loaded to the FTIR Spectrophotometer and scanned between 4000 to 400 cm$^{-1}$. The data was processed using Spectrum One Software.

Figure 11:
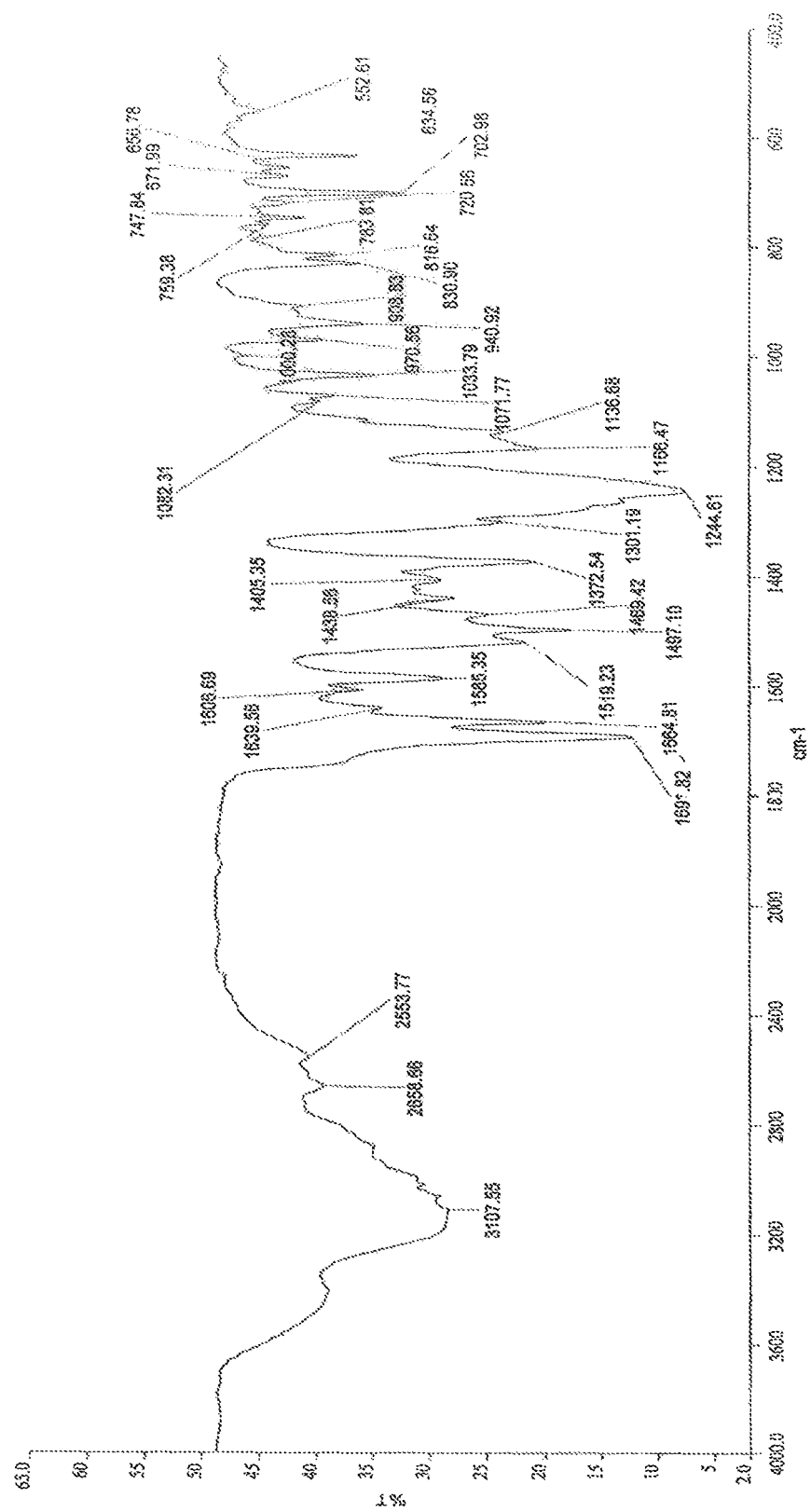
FIG. 11 shows a Fourier transform infrared (FTIR) spectrum of a lumacaftor ethyl acetate solvate as prepared by methods disclosed herein.

Within the context of this embodiment, the crystalline lumacaftor ethyl acetate solvate prepared by methods disclosed herein may be characterized by the FTIR spectrum in FIG. 11. Within the context of this embodiment, the lumacaftor ethyl acetate solvate may be further characterized by an FTIR spectrum having a characteristic peak at 1741 cm$^{-1}$.

The purity of the lumacaftor solvates disclosed herein may be analyzed by HPLC. Therefore, crystalline lumacaftor acetic acid solvate and crystalline lumacaftor ethyl acetate solvate were analyzed by HPLC. The lumacaftor ethyl acetate solvate and lumacaftor acetic acid solvate prepared according to methods disclosed herein may exhibit a purity of 99% or greater.

Amorphous lumacaftor, the crystalline lumacaftor acetic acid solvate, and the crystalline lumacaftor ethyl acetate solvate disclosed herein may exhibit long-term physical and chemical stability. The physical and chemical stabilities of the crystalline lumacaftor acetic acid solvate and the crystalline lumacaftor ethyl acetate solvate were determined by storing samples of each at 40° C./75% relative humidity (RH) and at 25° C./60% RH for six months. The samples were tested for stability by PXRD analysis and for purity by HPLC analysis.

As an example, Table 1 below provides data collected on amorphous lumacaftor. The stability data demonstrate that amorphous lumacaftor displays no significant chemical degradation and no change in PXRD pattern when stored for 3 months at 5±3° C. and 25° C./60% relative humidity (RH) conditions.

TABLE 1

| | Amorphous lumacaftor | |
|---|---|---|
| Storage condition | HPLC Purity (%) | PXRD |
| at 25° C./60% RH | | |
| Initial | 99.65 | Amorphous |
| 15 days | 99.67 | Stable |
| 1 months | 99.63 | Stable |
| 2 months | 99.60 | Stable |
| 3 months | 99.65 | Stable |
| at 5 ± 3° C. | | |
| Initial | 99.65 | Amorphous |
| 15 days | 99.67 | Stable |
| 1 months | 99.61 | Stable |
| 2 months | 99.63 | Stable |
| 3 months | 99.64 | Stable |

As another example, Table 2 below provides data collected on crystalline lumacaftor ethyl acetate solvate and the crystalline lumacaftor acetic acid solvate. The stability data demonstrate that neither the lumacaftor ethyl acetate solvate nor the lumacaftor acetic acid solvate display any significant chemical degradation or any change in PXRD pattern when stored for 6 months at 25° C./60% and 40° C./75% relative humidity (RH) conditions.

TABLE 2

| | Solvate | | | |
|---|---|---|---|---|
| | Lumacaftor ethyl acetate solvate | | Lumacaftor acetic acid solvate | |
| Condition | HPLC Purity (%) | PXRD | HPLC Purity (%) | PXRD |
| at 40° C./75% RH | | | | |
| Initial | 99.97 | Crystalline | 99.84 | Crystalline |
| 15 days | 99.95 | Stable | 99.92 | Stable |
| 1 months | 99.94 | Stable | 99.93 | Stable |
| 2 months | 99.95 | Stable | 99.93 | Stable |
| 3 months | 99.95 | Stable | 99.89 | Stable |
| 6 months | 99.95 | Stable | 99.92 | Stable |
| at 25° C./60% RH | | | | |
| Initial | 99.97 | Crystalline | 99.84 | Crystalline |
| 15 days | 99.95 | Stable | 99.92 | Stable |
| 1 months | 99.93 | Stable | 99.92 | Stable |
| 2 months | 99.95 | Stable | 99.92 | Stable |
| 3 months | 99.92 | Stable | 99.89 | Stable |
| 6 months | 99.95 | Stable | 99.93 | Stable |

The amorphous lumacaftor, the crystalline lumacaftor acetic acid solvate, the crystalline lumacaftor ethyl acetate solvate, and the amorphous solid dispersion of lumacaftor as disclosed herein may be included in pharmaceutical dosage forms for administration to patients in need thereof. Biochemically, lumacaftor may act as a chaperone during protein folding and may increase the number of cystic fibrosis transmembrane conductance regulator (CFTR) proteins trafficked to the cell surface. Accordingly, the lumacaftor forms disclosed herein may be useful in treating CFTR-mediated diseases in patients, either alone or in combination with other active pharmaceutical agents, for example, with lumacaftor. The amorphous lumacaftor, the crystalline lumacaftor acetic acid solvate, the crystalline lumacaftor ethyl acetate solvate, and the amorphous solid dispersion of lumacaftor as disclosed herein may be combined with pharmaceutically acceptable excipients in generating an oral dosage form, such as a tablet or capsule. Such excipients may include microcrystalline cellulose, croscarmellose sodium, hypromellose acetate succinate, magnesium stearate, povidone, and sodium lauryl sulfate. The oral dosage form may further be coated with a film that may include excipients such as carmine, FD&C Blue #1, FD&C Blue #2, polyethylene glycol, polyvinyl alcohol, talc, titanium dioxide, ammonium hydroxide, iron oxide black, shellac, artificial colors, artificial flavorings, or mixtures thereof. The oral dosage form may include an effective amount of lumacaftor, for example, an amount equivalent to 200 milligrams of the lumacaftor API.

Certain specific aspects and embodiments of the present application will be explained in greater detail with reference to the following examples, which are provided only for purposes of illustration and should not be construed as limiting the scope of the disclosure in any manner. Reasonable variations of the described procedures are intended to be within the scope of the present application. While particular aspects of the present application have been illustrated and described, it would be apparent to those skilled in the art that various other changes and modifications can be made without departing from the spirit and scope of the disclosure. It is therefore intended to encompass all such changes and modifications that are within the scope of this disclosure.

EXAMPLES

Example 1: Preparation of Amorphous Lumacaftor

Lumacaftor (2.5 g) was dissolved in methanol (100 mL) at 60-65° C. and cooled to 25-30° C. The solution was then filtered through Hyflo to remove any undissolved particulate. The clear solution was then subjected to spray drying in a laboratory spray dryer (Model Buchi-290) with a feed rate of the solution 15 mL/min and inlet temperature at 75° C. and with 100% aspiration to yield amorphous lumacaftor.

Example 2: Preparation of Amorphous Solid Dispersion of Lumacaftor

Lumacaftor (5.0 g) and Povidone K-30 (5.0 g) were dissolved in methanol (230 mL) at 65° C. The clear solution was filtered through Hyflo to remove any undissolved particulate. The clear filtrate was subjected to spray-drying in a laboratory spray dryer (Model Buchi-290) with a feed rate of the solution 15 mL/min and inlet temperature of 75° C. with 100% aspiration to yield an amorphous solid dispersion of lumacaftor with Povidone K-30.

Example 3: Preparation of Amorphous Solid Dispersion of Lumacaftor

Lumacaftor (9.0 g) and Povidone K-30 (1.0 g) were dissolved in methanol (440 mL) at 65° C. The clear solution was filtered through Hyflo to remove any undissolved particulate. The clear filtrate was subjected to spray drying in a laboratory spray dryer (Model Buchi-290) with a feed rate of the solution 15 mL/min and inlet temperature of 75° C. with 100% aspiration to yield an amorphous solid dispersion of lumacaftor with Povidone K-30.

Example 4: Preparation of Amorphous Solid Dispersion of Lumacaftor

Lumacaftor (5.0 g) and Plasdone S-630 (5.0 g) were dissolved in methanol (230 mL) at 65° C. The clear solution was filtered through Hyflo to remove any undissolved particulate. The clear filtrate was subjected to spray drying in a laboratory spray dryer (Model Buchi-290) with a feed rate of the solution 15 mL/min and inlet temperature of 75° C. with 100% aspiration to yield an amorphous solid dispersion of lumacaftor with Plasdone S-630.

Example 5: Preparation of Amorphous Solid Dispersion of Lumacaftor

Lumacaftor (9.0 g) and Plasdone S-630 (1.0 g) were dissolved in methanol (440 mL) at 65° C. The clear solution was filtered through Hyflo to remove any undissolved particulate. The clear filtrate was subjected to spray drying in a laboratory spray dryer (Model Buchi-290) with a feed rate of the solution 15 mL/min and inlet temperature of 75° C. with 100% aspiration to yield an amorphous solid dispersion of lumacaftor with Plasdone S-630.

Example 6: Preparation of Lumacaftor Acetic Acid Solvate

Lumacaftor (5 g) was suspended in acetic acid (95-98%, 25 mL) at 25-30° C. and maintained under agitation for two days. The slurry was filtered and the solid was washed with ice cold water. The obtained solid was dried at 40° C. for 12 hours to yield crystalline lumacaftor acetic acid solvate.

Example 7: Preparation of Lumacaftor Acetic Acid Solvate

Lumacaftor (1 g) was dissolved in acetic acid (95-98%, 8 mL) at 75° C. The clear solution was filtered at 75° C. to remove any undissolved particulate through Hyflo (1 g) and washed with acetic acid (75° C., 2 mL). The clear solution of lumacaftor was cooled to 25° C. and stirred over 48 hours at 25° C. The solid obtained was filtered, washed with ice cold water (10 mL), and dried at 40° C. under vacuum for 12 hours. The resulting product was identified as a lumacaftor acetic acid solvate.

Example 8: Preparation of Lumacaftor Ethyl Acetate Solvate

Lumacaftor (1 g) was dissolved in ethyl acetate (18 mL) at 70° C. The solution was filtered at 70° C. to remove undissolved particulate and then cooled to −20° C. over 10-30 minutes. The clear solution of lumacaftor was stirred at −20° C. for 15 hours. The solid obtained was filtered, washed with chilled ethyl acetate (5 mL), and dried at 40° C. under vacuum for 3 hours. The resulting product was identified as a lumacaftor ethyl acetate solvate.

Yield=0.66 g

Example 9: Preparation of Ethyl Acetate Solvate of Lumacaftor

Lumacaftor (0.1 g) was dissolved in ethyl acetate (1.8 mL) at 70° C. The solution was filtered at 70° C. to remove undissolved particulate. Heptane (1.8 mL) was added and the clear solution was cooled to −20° C. over 10-30 minutes. The clear solution of lumacaftor was stirred at −20° C. for 3 hours. The solution was filtered to obtain a solid, which was washed with chilled heptane (1 mL) and dried at 40° C. under vacuum for 3 hours. The resulting product was identified as a lumacaftor ethyl acetate solvate.

Yield=0.070 g.

We claim:

1. A crystalline lumacaftor acetic acid solvate.
2. The crystalline lumacaftor acetic acid solvate of claim 1, characterized by a $^1$H NMR (300 MHz, DMSO-d6) spectrum having peaks at 8.99, 7.97-7.89, 7.73-7.70, 7.69-7.67, 7.57-7.52, 7.38-7.34, 7.33-7.30, 2.22, 1.91, 1.52-1.48, and 1.16-1.13.
3. The crystalline lumacaftor acetic acid solvate of claim 1, characterized by a PXRD pattern as shown in FIG. 3.
4. Crystalline lumacaftor acetic acid solvate according to claim 1, with a purity of at least 99% as measured by HPLC.
5. A process for the preparation of a crystalline lumacaftor acetic acid solvate comprising the steps of either:
   a) suspending lumacaftor in acetic acid solvent; and
   b) isolating the crystalline lumacaftor acetic acid solvate;
   or
   a) dissolving lumacaftor in acetic acid solvent to form a solution
   b) cooling the solution; and
   c) isolating crystalline lumacaftor acetic acid solvate.

* * * * *